United States Patent
Uyttendaele et al.

(10) Patent No.: US 6,310,001 B1
(45) Date of Patent: *Oct. 30, 2001

(54) SUBSTANTIALLY LIGHT-INSENSITIVE THERMOGRAPHIC RECORDING MATERIALS WITH IMPROVED STABILITY

(75) Inventors: Carlo Uyttendaele; Jan Gilleir, both of Mortsel; Ingrid Geuens, Emblem; Ivan Hoogmartens, Wilrijk, all of (BE)

(73) Assignee: Agfa-Gevaert, Mortsel (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/153,879

(22) Filed: Sep. 15, 1998

(30) Foreign Application Priority Data

| Sep. 17, 1997 | (EP) | 97202871 |
| Sep. 17, 1997 | (EP) | 97202872 |
| Sep. 17, 1997 | (EP) | 97202873 |
| Sep. 17, 1997 | (EP) | 97202875 |
| Sep. 17, 1997 | (EP) | 97202876 |
| Sep. 17, 1997 | (EP) | 97202877 |
| Dec. 6, 1997 | (EP) | 97203833 |
| Dec. 6, 1997 | (EP) | 97203834 |
| Jun. 6, 1998 | (EP) | 98201963 |

(51) Int. Cl.[7] .................................... B41M 5/20
(52) U.S. Cl. ............... 503/202; 428/212; 503/210
(58) Field of Search ................................ 428/396, 195, 428/478.2, 212, 146, 152; 430/350, 510, 572, 523, 584, 588, 619, 944; 427/46, 152; 503/202, 210, 212

(56) References Cited

U.S. PATENT DOCUMENTS 5,851,755 * 12/1998 Uyttenhoeven et al. ............. 430/619
5,958,667 * 9/1999 Dercoover et al. ................... 430/584

* cited by examiner

Primary Examiner—Bruce H. Hess
Assistant Examiner—Michael E. Grendzynski
(74) Attorney, Agent, or Firm—Baker Botts L.L.P.

(57) ABSTRACT

A substantially light-insensitive thermographic recording material substantially exclusive of cationic surfactants in which at least one non-cationic surfactant is present, the thermographic recording material comprising a support and a thermosensitive element containing a substantially light-insensitive organic silver salt, a reducing agent therefor in thermal working relationship therewith and a binder, wherein all the non-cationic surfactants present in the thermographic recording material together have a non-fluorohalide ion concentration of 1500 ppm or less; and a process for the production thereof.

12 Claims, No Drawings

US 6,310,001 B1

SUBSTANTIALLY LIGHT-INSENSITIVE THERMOGRAPHIC RECORDING MATERIALS WITH IMPROVED STABILITY

FIELD OF THE INVENTION

The present invention relates to a substantially light-insensitive thermographic recording material with improved stability.

BACKGROUND OF THE INVENTION

Thermography is concerned with materials which are substantially light-insensitive, but are sensitive to heat or thermographic. Most of the "direct" thermographic recording materials are of the chemical type. On heating to a certain conversion temperature, an irreversible chemical reaction takes place and a coloured image is produced. A wide variety of chemical systems has been suggested some examples of which have been given on page 138 of the book "Imaging Systems" by Kurt I. Jacobson-Ralph E. Jacobson, The Focal Press—London and New York (1976), describing the production of a silver metal image by means of a thermally induced oxidation-reduction reaction of a silver soap with a reducing agent.

In U.S. Pat. No. 2,910,977 the following statement is made in the description in column 7, lines 23–27: "Stability towards exposure to light is improved by selecting highly purified materials; freedom from halides and sulfides is particularly important in the case of compositions involving silver salts." The disclosure in U.S. Pat. No. 2,910,977 concerned thermographic recording materials coated from solvent media.

WO 94/16361 discloses a multilayer heat-sensitive material which comprises: a colour-forming layer comprising: a colour-forming amount of finely divided, solid colourless noble metal or iron salt of an organic acid distributed in a carrier composition; a colour developing amount of a cyclic or aromatic organic reducing agent, which at thermal copy and printing temperatures is capable of a colour-forming reaction with the noble metal or iron salt; and an image-toning agent; characterized in that (a) the carrier composition comprises a substantially water-soluble polymeric carrier and a dispersing agent for the noble metal or iron salt and (b) the material comprises a protective overcoating layer for the colour-forming layer.

Coating of thermographic recording materials from aqueous media is preferred over coating from solvent for ecological and economic reasons. However, the inventors of the present invention found that the choice of surfactants used in the production of thermographic recording materials using aqueous dispersions and solutions had a substantial effect upon the stability of the thermographic recording materials produced and on prints produced therewith.

OBJECTS OF THE INVENTION

It is therefore an object of the present invention to provide thermographic recording materials coated from aqueous media which exhibit improved stability.

It is therefore another object of the present invention to provide thermographic recording materials which are capable of producing thermographic prints which exhibit improved stability.

Further objects and advantages of the invention will become apparent from the description hereinafter.

SUMMARY OF THE INVENTION

In view of the statement made in U.S. Pat. No. 2,910,977 to the effect that freedom from halides is particularly important it is surprising that the halide concentration in the totality of surfactants present in thermographic recording materials coated from aqueous media can be as high as 500 ppm without adversely affected the light-stability of thermographic recording materials coated from aqueous media.

A substantially light-insensitive thermographic recording material substantially exclusive of cationic surfactants is provided in which at least one non-cationic surfactant is present, the thermographic recording material comprising a support and a thermosensitive element containing a substantially light-insensitive organic silver salt, a reducing agent therefor in thermal working relationship therewith and a binder, wherein all the non-cationic surfactants present in the thermographic recording material together have a non-fluoro-halide ion concentration of 1500 ppm or less.

A process for producing the substantially light-insensitive thermographic recording material referred to above is also provided comprising the steps of: producing an aqueous dispersion of the substantially light-insensitive organic silver salt; producing one or more aqueous coating compositions containing together the aqueous dispersion of the substantially light-insensitive organic silver salt, the reducing agent and the binder; and applying the one or more aqueous coating compositions to the support thereby forming after drying the thermosensitive element, characterized in that one or more of the aqueous dispersion of the substantially light-insensitive organic silver salt and the one or more aqueous coating compositions aqueous contain a non-cationic surfactant.

Preferred embodiments of the present invention are disclosed in the detailed description of the invention.

DETAILED DESCRIPTION OF THE INVENTION

In a preferred embodiment the substantially light-insensitive thermographic recording materials of the present invention are black and white thermographic recording materials.

Aqueous

The term aqueous for the purposes of the present invention includes mixtures of water with water-miscible organic solvents such as alcohols e.g. methanol, ethanol, 2-propanol, butanol, iso-amyl alcohol etc.; glycols e.g. ethylene glycol; glycerine; N-methyl pyrrolidone; methoxypropanol; and ketones e.g. 2-propanone and 2-butanone etc.

Substantially

By substantially light-insensitive is meant not intentionally light sensitive. By substantially solvent-free aqueous medium is meant that solvent, if present, is present in amounts below 10% by volume of the aqueous medium.

Non-cationic Surfactants

Surfactants are surface active agents which are soluble compounds which reduce the interfacial tension between a liquid and a solid. Cationic surfactants have not been found to be useful for this application due to their photographic activity and the use of halide counterions in most commercial surfactants.

Non-cationic surfactants aid the dispersion of ingredients which are insoluble in the particular dispersion medium. The thermographic recording materials of the present invention contain at least one non-cationic surfactant, which may be anionic, non-ionic or amphoteric.

In the present invention the expression: "all the non-cationic surfactants present in the thermographic recording material together have a particular non-fluoro-halide ion concentration in ppm's", means 10 multiplied by the sum of the quantities of non-fluoro-halide ions in the different non-cationic surfactants present divided by the sum of the quantities of all the non-cationic surfactants present in the same units of weight as that used for the quantities of non-fluoro-halide ions.

In a preferred embodiment of the present invention all the non-cationic surfactants present in the thermographic recording material together have a non-fluoro-halide ion concentration of 1000 ppm or less, with 500 ppm or less being particularly preferred and 200 ppm being especially preferred. It is also preferred that all the non-cationic surfactants present in the thermographic recording material together have an alkali metal ion concentration of 200 ppm or less. The alkali metal ions are: sodium, potassium, lithium, rubidium and caesium.

The chloride ion and sodium ion concentrations determined by ionic chromatography for commercial non-cationic surfactants according to the present invention are given in table 1.

Surfactant Nr. S09=ARKOPAL™ N060 (previously HOSTAPAL™ W), a nonylphenylpolyethylene-glycol from HOECHST.

Surfactant Nr. S10=GAFAC™ RM710, a complex organic phosphate ester from GAF.

Surfactant Nr. S11=ALKANOL™ XC, supplied as a 90% concentrate of a sodium nonylnaphthalene-sulfonate by DU PONT;

Surfactant Nr. S12=sodium dodecyl sulphate;

Surfactant Nr. S13=DOWFAX™ 2A1, supplied as a 45% concentrate of a disodium salt of di(decyl-sulfo-phenyl) ether by DOW CORNING;

Surfactant Nr. S14=NIAPROOF ANIONIC™ 4, supplied as a 27% concentrate of a sodium 1-(2'-ethylbutyl)-4-ethylhexylsulphate by NIACET;

Surfactant Nr. S15=HOSTA, supplied as a 95% concentrate of purified sodium salt of N-methyl-N-2-sulfoethyl-oleylamide, from HOECHST;

Surfactant Nr. S16=MERSOLAT™ H76 (previously MERSOLAT™ H80), supplied as a 76% concentrate of a sodium pentadecylsulfonate by BAYER;

Surfactant Nr. S17=HOSTAPON™ T, supplied as a 40% concentrate of a sodium salt of N-methyl-N-2-sulfoethyl-oleylamide by HOECHST;

TABLE 1

| Surfactant Nr | Type | SURFACTANT | [Cl$^-$] [ppm] | [Na$^+$] [ppm] |
|---|---|---|---|---|
| S01 | A | HOSTAPAL ™ B | <50 | |
| S02 | A | MARLON ™ A365 | <40 | 4300 |
| S03 | A | dodecyl sulfonic acid | <40 | <1000 |
| S04 | A | ULTRAVON ™ W | 700 | 74468 |
| S05 | A | HOSTAPUR ™ SAS 60 | <40 | |
| S06 | A | MARLON ™ AS3 | <200 | <200 |
| S07 | N | ANTAROX ™ CO 880 | <40 | |
| S08 | N | SURFYNOL ™ CT111 | <40 | |
| S09 | N | ARKOPAL ™ N 060 | <20 | |
| S10 | N | GAFAC ™ RM 710 | <40 | <1000 |
| S11 | A | ALKANOL ™ XC | 1600 | |
| S12 | A | sodium dodecyl sulfate | 6400 | |
| S13 | A | DOWFAX ™ 2A1 | 2700 | |
| S14 | A | NIAPROOF ™ ANIONIC 4 | 7800 | |
| S15 | A | HOSTA ™ | 5970 | |
| S16 | A | MERSOLAT ™ H76 | 17000 | |
| S17 | A | HOSTAPON ™ T | 84000 | |
| S18 | N | AKYPO ™ OP80) | 3442 | 1338 |
| S19 | N | AKYPO ™ RLM 45 | 2700 | |

A: anionic
N: non-ionic

Surfactant Nr. S01=HOSTAPAL™ B. supplied as a 50% concentrate of a sodium trisalkylphenyl-polyethyleneglycol(EO 7-8)sulphate by HOECHST;

Surfactant Nr. S02=MARLON™ A-365, supplied as a 65% concentrate of a sodium alkyl-phenylsulfonate by H ÜGLS;

Surfactant Nr. S03=4-dodecylbenzene sulfonic acid from

Surfactant Nr. S04=ULTRAVON™ W, supplied as a 75–85% concentrate of a sodium arylsulfonate by CIBA-GEIGY;

Surfactant Nr. S05=HOSTAPUR™SAS, supplied as a 60% concentrate of a secondary alkanesulfonate by HOECHST;

Surfactant Nr. S06=MARLON™ AS3, supplied as a 98% concentrate of an alkylphenylsulfonic acid by HÜLS;

Surfactant Nr. S07=ANTAROX™ CO 880,a nonyl-phenyl-oxy-polyethyleneglycol(EO 30), from GAF;

Surfactant Nr. S08=SURFYNOL™ CT111, a nonionic surfactant supplied by AIR PRODUCTS;

Surfactant Nr. S18=AKYPO™ OP80, supplied as an 80% concentrate of an octyl-phenyl-oxy-polyethyleneglycol (EO 8)acetic acid by CHEMY;

Surfactant Nr. S19=AKYPO™ RLM45, supplied as a 85% concentrate of a monoethanolamine salt of a polyethylene-glycol-substituted fatty acid, by CHEMY.

It is evident that according to the thermographic recording materials of the present invention, surfactants S11 to S19 can only be used in combination with much larger quantities of sufactants with much lower chloride ion concentration, so that the overall chloride ion concentration in the surfactants present does not exceed 500 ppm.

Thermosensitive Element

According to the present invention, a substantially light-insensitive thermographic recording material is provided comprising a thermosensitive element including a substantially light-insensitive organic silver salt, an organic reducing agent therefor in thermal working relationship therewith and a binder. The element may comprise a layer system in which the ingredients are dispersed in different layers, with the proviso that the substantially light-insensitive organic silver salt and the organic reducing agent are in thermal working relationship with one another i.e. during the thermal development process the reducing agent must be present in such a way that it is able to diffuse to the substantially light-insensitive organic silver salt particles so that reduction of the organic silver salt can take place. The thickness of the thermosensitive element is preferably in the range of 1 to 50 μm.

Organic Silver Salts

Preferred substantially light-insensitive organic silver salts used in the present invention are silver salts of aliphatic carboxylic acids known as fatty acids, wherein the aliphatic carbon chain has preferably at least 12 C-atoms, e.g. silver laurate, silver palmitate, silver stearate, silver hydroxystearate, silver oleate and silver behenate, which silver salts are also called "silver soaps". Silver salts of modified aliphatic carboxylic acids with thioether group as described e.g. in GB-P 1,111,492 and other organic silver salts as described in GB-P 1,439,478, e.g. silver benzoate, may likewise be used to produce a thermally developable silver image. Combinations of different organic silver salts may also be used in the present invention.

Preparation of aqueous dispersions of silver behenate-containing particles in the substantial absence of solvent The aqueous dispersion of the substantially light-insensitive salt is preferably produced using a production process for a dispersion of particles of substantially light-insensitive organic silver salt including silver behenate in an aqueous medium comprising the steps of: i) producing an aqueous dispersion of one or more organic acids including behenic acid and a salt of an alkylarylsulfonate; ii) substantially neutralizing the organic acids with aqueous alkali thereby forming organic acid salts including a behenic acid salt; (iii) adding an aqueous solution of a silver salt to completely convert the organic acid salts into their silver salts including silver behenate, characterized in that the anionic surfactant is present in a molar ratio with respect to organic acid greater than 0.15 and the silver salt is added at a rate between 0.025 mol/mol organic silver salt-min and 2.25 mol/mol organic silver salt-min. In preferred embodiments of the production process for a dispersion of particles of substantially light-insensitive organic silver salt including silver behenate in an aqueous medium the anionic surfactant is present in a molar ratio with respect to organic carboxylic acid greater than 0.25 and the silver salt is added at a rate between 0.03 mol/mol organic silver salt-min and 0.7 mol/mol organic silver salt-min, with a molar ratio of anionic surfactant with respect to organic acid greater than 0.3 and a rate of silver salt addition of between 0.04 mol/mol organic silver salt-min and 0.3 mol/mol organic silver salt-min being particularly preferred.

In a preferred embodiment step (iii) of the production process of the present invention is carried out such that part the solution of acid salts produced in step (ii) of the process is present in the reaction vessel prior to silver salt solution addition and part thereof is added simultaneously with the addition of the silver salt solution, with about 25 to 50% of the solution of acid salts produced in step (ii) being in the reaction vessel prior to silver salt addition being particularly preferred.

The above-described production process for a dispersion of particles of substantially light-insensitive organic silver salt including silver behenate in an aqueous medium the pH used must be sufficiently low to avoid the oxidation of silver ions to silver oxide or silver hydroxide for which a pH below 10 is usually required, the process temperature is chosen such that it is above the melting point of the organic acid(s) used which in the case of behenic acid means a temperature of about 80 to 85° C., must be carried out with stirring, the stirring rate being dependent upon the size of the stirrer relative to the reaction vessel, the type of stirrer used, avoidance of silver oxide or silver hydroxide formation due to insufficient mixing and avoidance of foaming, and being usually between 200 and 1000 rpm and a slight excess of an organic acid, for example behenic acid with e.g. 2 mol % excess being preferred.

The size of the silver acid salts particles containing silver behenate can be varied by varying the rate of silver salt addition, the concentration of anionic surfactant and the temperature, the equivalent diameter of the particles increasing with decreasing addition rate, decreasing anionic surfactant concentration and increasing temperature.

Film-forming Binders of the Thermosensitive Element

The layer containing the organic silver salt is applied from an aqueous medium containing a water-dispersible binder and/or a water dispersible binder.

Suitable water-soluble film-forming binders for use in thermosensitive element according to the present invention are: polyvinyl alcohol, polyacrylamide, polymethacrylamide, polyacrylic acid, polymethacrylic acid, polyvinylpyrrolidone, polyethyleneglycol, proteinaceous binders such as gelatin, modified gelatins such as phthaloyl gelatin, polysaccharides, such as starch, gum arabic and dextran and water-soluble cellulose derivatives. A preferred water-soluble binder for use in the thermographic and photothermographic recording materials of the present invention is gelatin.

Suitable water-dispersible binders for use in the thermographic and photothermographic recording materials of the present invention may be any water-insoluble polymer It should be noted that there is no clear cut transition between a polymer dispersion and a polymer solution in the case of very small polymer particles resulting in the smallest particles of the polymer being dissolved and those slightly larger being in dispersion. Preferred water-dispersible binders for use according to the present invention are water-dispersible film-forming polymers with covalently bonded ionic groups selected from the group consisting of sulfonate, sulfinate, carboxylate, phosphate, quaternary ammonium, tertiary sulfonium and quaternary phosphonium groups. Further preferred water-dispersible binders for use according the the present invention are water-dispersible film-forming polymers with covalently bonded moieties with one or more acid groups.

The weight ratio of binder used according to the present invention to organic silver salt weight is preferably in the range of 0.2 to 6.

Thermal Solvents

The above mentioned binders or mixtures thereof may be used in conjunction with waxes or "heat solvents" also called "thermal solvents" or "thermosolvents" improving the reaction speed of the redox-reaction at elevated temperature. By the term "heat solvent" in this invention is meant a non-hydrolyzable organic material which is in a solid state in the recording layer at temperatures below 50° C., but upon heating becomes a plasticizer for the recording layer and/or a liquid solvent for at least one of the redox-reactants.

Organic Reducing Agents

Suitable organic reducing agents for the reduction of organic silver salt particles containing silver stearate are organic compounds containing at least one active hydrogen atom linked to O, N or C, such as is the case with, aromatic di- and tri-hydroxy compounds; aminophenols; METOL (tradename); p-phenylene-diamines; alkoxynaphthols, e.g. 4-methoxy-1-naphthol described in U.S. Pat. No. 3,094,41; pyrazolidin-3-one type reducing agents, e.g. PHENIDONE (tradename); pyrazolin-5-ones; indan-1,3-dione derivatives; hydroxytetrone acids; hydroxytetronimides; hydroxylamine derivatives such as for example described in U.S. Pat. No. 4,082,901; hydrazine derivatives; and reductones e.g. ascorbic acid; see also U.S. Pat. Nos. 3,074,809, 3,080,254, 3,094,417 and 3,887,378.

Catechol-type reducing agents, i.e. reducing agents containing at least one benzene nucleus with two hydroxy groups (—OH) in ortho-position, such as catechol, 3-(3,4-dihydroxyphenyl) propionic acid, 1,2-dihydroxybenzoic acid, gallic acid and esters e.g. methyl gallate, ethyl gallate, propyl gallate, tannic acid, and 3,4-dihydroxy-benzoic acid esters are preferred, with those described in EP-B 692 733 and unpublished European Patent Application EP 97202872.4 being particularly preferred. Other suitable reducing agents are sterically hindered phenols, bisphenols and sulfonamidophenols.

Combinations of reducing agents may also be used that on heating become reactive partners in the reduction of the substantially light-insensitive organic silver salt containing silver stearate. For example, combinations of reducing agents with sulfonamidophenols are described in the periodical Research Disclosure, February 1979, item 17842, in U.S. Pat. No. 4,360,581 and 4,782,004, and in EP-A 423 891 and combinations of sterically hindered phenols with sulfonyl hydrazide reducing agents such as disclosed in U.S. Pat. No. 5,464,738; trityl hydrazides and formyl-phenyl-hydrazides such as disclosed in U.S. Pat. No. 5,496,695; trityl hydrazides and formyl-phenyl-hydrazides with diverse auxiliary reducing agents such as disclosed in U.S. Pat. No. 5,545,505, U.S. Pat. No. 5.545.507 and U.S. Pat. No. 5,558,983; acrylonitrile compounds as disclosed in U.S. Pat. No. 5,545,515 and U.S. Pat. No. 5,635,339; and 2-substituted malonodialdehyde compounds as disclosed in U.S. Pat. No. 5,654,130. Organic reducing metal salts, e.g. stannous stearate, have also been used in such reducing agent combinations, as disclosed in U.S. Pat. No. 3,460,946 and 3,547,648, as have sterically hindered phenols and bisphenols, as described in U.S. Pat. No. 4,001,026 and U.S. Pat. No. 3,547,648 respectively.

Toning Agents

In order to obtain a neutral black image tone in the higher densities and neutral grey in the lower densities, thermographic recording materials according to the present invention may contain one or more toning agents. The toning agents should be in thermal working relationship with the substantially light-insensitive organic silver salt and reducing agents during thermal processing. Any known toning agent from thermography or photothermography may be used. Suitable toning agents are the phthalimides and phthalazinones within the scope of the general formulae described in U.S. Pat. No. 4,082,901 and the toning agents described in U.S. Pat. No. 3,074,809, U.S. Pat. No. 3,446,648 and U.S. Pat. No. 3,844,797. Particularly useful toning agents are the heterocyclic toner compounds of the benzoxazine dione or naphthoxazine dione type described in GB-P 1,439,478, U.S. Pat. No. 3,951,660 and U.S. Pat. No. 5,599,647.

Dispersants

Suitable dispersants are natural polymeric substances, synthetic polymeric substances and finely divided powders, for example finely divided non-metallic inorganic powders such as silica.

Stabilizers and Antifoggants

In order to obtain improved shelf-life and reduced fogging, stabilizers and antifoggants may be incorporated into the thermographic recording materials of the present invention.

Polycarboxylic Acids and Anhydrides Thereof

According to the recording material of the present invention the thermosensitive element may comprise in addition at least one polycarboxylic acid and/or anhydride thereof in a molar percentage of at least 15 with respect to all the organic silver salt(s) present and in thermal working relationship therewith. The polycarboxylic acid may be aliphatic (saturated as well as unsaturated aliphatic and also cycloaliphatic) or an aromatic polycarboxylic acid. These acids may be substituted e.g. with alkyl, hydroxyl, nitro or halogen. They may be used in anhydride form or partially esterified on the condition that at least two free carboxylic acids remain or are available in the heat recording step.

Other Ingredients

In addition to the ingredients the substantially light-insensitive thermographic recording material may contain other additives such as free fatty acids, silicone oil, ultraviolet light absorbing compounds, white light reflecting and/or ultraviolet radiation reflecting pigments, silica, and/or optical brightening agents.

Support

The support for the substantially light-insensitive thermographic recording material according to the present invention may be transparent, translucent or opaque and is preferably a thin flexible carrier made e.g. from paper, polyethylene coated paper or transparent resin film, e.g. made of a cellulose ester, e.g. cellulose triacetate, polypropylene, polycarbonate or polyester, e.g. polyethylene terephthalate. The support may be in sheet, ribbon or web form. The support may be made of an opacified resin composition.

Subbing layer between the support and the thermosensitive element

A subbing layer may also be provided between the support and the thermosensitive element. In a preferred embodiment the subbing layer contains a binder, less than 20% by weight of silica and covalently bonded acid groups in the binder, if present, are either substantially present as free acid or substantially present as acid salts. In a further preferred embodiment the subbing layer contains a non-cationic surfactant.

It is particularly preferred that the subbing layer used in the thermographic recording materials of the present invention contain less than 40 ppm of free choride ions, with less than 10 ppm of free chloride ions being especially preferably.

Preferred ingredients for the subbing layer used in the thermographic recording materials of the present invention are a polymer latex, polyethylene wax and hydrolyzed polyalkoxysilanes. By the term polyalkoxysilane is meant a silane with a least two hydrolyzable alkoxy-groups.

Protective Layer

A protective layer may also be provided for the thermosensitive element. In a preferred embodiment this protective layer contains a non-cationic surfactant. In general the protective layer protects the thermosensitive element from atmospheric humidity and from surface damage by scratching etc. and prevents direct contact of printheads or heat sources with the recording layers. Protective layers for thermosensitive elements which come into contact with and have to be transported past a heat source under pressure, have to exhibit resistance to local deformation and good slipping characteristics during transport past the heat source during heating.

The protective layer may comprise a dissolved lubricating material and/or particulate material, e.g. talc particles, optionally protruding therefrom. Examples of suitable lubricating materials are a surface active agent, a liquid lubricant, a solid lubricant or mixtures thereof, which may be used with or without a polymeric binder. Suitable slipping layer compositions are described, for example, in U.S. Pat. No. 5,587,350, U.S. Pat. No. 5,536,696, U.S. Pat. No. 5,547,914, WO 95/12495, EP-A 775 592 and EP-A 775 595.

Coating

The coating of any layer of the substantially light-insensitive thermographic recording materials of the present invention may proceed by any coating technique e.g. such as described in Modern Coating and Drying Technology, edited by Edward D. Cohen and Edgar B. Gutoff, (1992) VCH Publishers Inc., 220 East 23rd Street, Suite 909 New York, N.Y. 10010, USA.

Thermographic Printing

Thermographic imaging is carried out by the image-wise application of heat either in analogue fashion by direct exposure through an image of by reflection from an image, or in digital fashion pixel by pixel either by using an infra-red heat source, for example with a Nd-YAG laser or other infra-red laser, or by direct thermal imaging with a thermal head.

In thermal printing, image signals are converted into electric pulses and then through a driver circuit selectively transferred to a thermal printhead. The thermal printhead consists of microscopic heat resistor elements, which convert the electrical energy via the Joule effect into heat, which is transferred to the surface of the thermographic recording material wherein the chemical reaction resulting in the development of a black and white image takes place. Such thermal printing heads may be used in contact or close proximity with the recording layer. The operating temperature of common thermal printheads is in the range of 300 to 400° C. and the heating time per picture element (pixel) may be less than 1.0 ms, the pressure contact of the thermal printhead with the recording material being e.g. 200–500 g/cm to ensure a good transfer of heat.

In order to avoid direct contact of the thermal printing heads with a recording layer not provided with an outermost protective layer, the image-wise heating of the recording layer with the thermal printing heads may proceed through a contacting but removable resin sheet or web wherefrom during the heating no transfer of recording material can take place.

The image signals for modulating the laser beam or current in the micro-resistors of a thermal printhead are obtained directly e.g. from opto-electronic scanning devices or from an intermediary storage means, optionally linked to a digital image work station wherein the image information can be processed to satisfy particular needs.

Activation of the heating elements can be power-modulated or pulse-length modulated at constant power. EP-A 654 355 describes a method for making an image by image-wise heating by means of a thermal head having energizable heating elements, wherein the activation of the heating elements is executed duty cycled pulsewise.

When used in thermographic recording operating with thermal printheads the thermographic recording materials are not suitable for reproducing images with fairly large number of grey levels as is required for continuous tone reproduction. EP-A 622 217 discloses a method for making an image using a direct thermal imaging element producing improvements in continuous tone reproduction.

Image-wise heating of the thermographic recording material can also be carried out using an electrically resistive ribbon incorporated into the material. Image- or pattern-wise heating of the thermographic recording material may also proceed by means of pixelwise modulated ultra-sound, using e.g. an ultrasonic pixel printer as described e.g. in U.S. Pat. No. 4,908,631.

Industrial Application

Substantially light-insensitive thermographic recording materials according to the present invention may be used for both the production of transparencies, for example in the medical diagnostic field in which black-imaged transparencies are widely used in inspection techniques operating with a light box, and reflection type prints, for example in the hard copy field. For such applications the support will be transparent or opaque, i.e. having a white light reflecting aspect. Should a transparent base be used, the base may be colourless or coloured, e.g. with a blue colour for medical diagnostic applications.

The following examples and comparative examples illustrate the present invention. The percentages and ratios used in the examples and compositions of the ingredients are by weight unless otherwise indicated.

i) subbing layer ingredients:
PAREZ RESIN™ 707: a 80% solids melamine-formaldehyde resin from AMERICAN CYANAMID;
HORDAMER™ PE02: a 40% aqueous dispersion of polyethylene from HOECHST;
R10985: a calcium-containing medium viscosity gelatin from ROUSSELOT;
KIESELSOL 100F: a 36% aqueous dispersion of colloidal silica from BAYER;
KIESELSOL 300F: a 30% aqueous dispersion of colloidal silica from BAYER;
PMMA: a 20% aqueous dispersion of polymethylmethacrylate particles 2 μm in diameter ii) thermosensitive element ingredients:
K7598=type 7598, a calcium-free gelatin from AGFA-GEVAERT GELATINEFABRIEK vorm. KOEPFF & SÖHNE;
K17881=type 17881, a calcium-free gelatin with low potassium ion, sodium ion and chloride-ion concentrations from AGFA-GEVAERT GELATINEFABRIEK vorm. KOEPFF & SÖHNE;
AgB=silver behenate
B79=BUTVAR- B79, a polyvinyl butyral from MONSANTO
R01=ethyl 3,4-dihydroxybenzoate, a reducing agent
T01=7-(ethylcarbonato)benzo[e][1,3]oxazine-2,4-dione, a toning agent T02=benzo[e][1,3]oxazine-2,4-dione, a toning agent Surfactant Nr. S19=ammonium dodecylphenylsulfonate with a Cl⁻ ion concentration below the detection limit of 20 ppm;

Surfactant Nr. S20=ammonium dodecylphenylsulfonate with 50 ppm Cl⁻;

Surfactant Nr. S21=ammonium dodecylphenylsulfonate with 200 ppm Cl⁻;

Surfactant Nr. S22=ammonium dodecylphenylsulfonate with 500 ppm Cl⁻; and the following latexes:

| polymer Latex nr | B [%] | IP [%] | BA [%] | S [%] | MMA [%] | IA [%] | MAA [%] | AA [%] |
|---|---|---|---|---|---|---|---|---|
| 1 # | 47.5 | — | — | — | 47.5 | 5 | — | — |
| 2 | 49 | — | — | — | 49 | 2 | — | — |
| 3 | — | 47.5 | — | — | 47.5 | 5 | — | — |
| 4 | — | — | 43 | 55 | — | 2 | — | — |
| 5 | — | — | 43 | 55 | — | — | 2 | — |
| 6 | — | — | 47 | 46 | — | — | 7 | — |
| 7 | — | — | 44 | 54 | — | — | 2 | — |
| 8 | — | — | 47.5 | 47.5 | — | — | — | 5 |
| 9 * | 50 | — | — | — | 50 | — | — | — | contains 1% of Surfactant Nr S01 versus monomers polymerized
* contains of 2% of Surf. Nr S04 & 0.8% of Surf. Nr S17 vs monomers polymerized where: B=butadiene; IP=isoprene; BA=butyl acrylate; EA=ethyl acrylate; S=styrene; MMA=methyl methacylate; IA=itaconic acid; MAA=methacrylic acid; and AA=acrylic acid.

INVENTION EXAMPLES 1 TO 10 AND COMPARATIVE EXAMPLES 1 & 2

Preparation of Subbing Layer 0.34 mm thick polyethylene terephthalate sheet was coated to a thickness of 0.1 mm with a composition which after drying and longitudinal and transverse stretching produced a 175 μm thick support coated on with the following subbing-layer composition expressed as the coating weights of the ingredients present:

| | |
|---|---|
| # copolymer of terephthalic acid/isophthalic acid/sulfo-isophthalic acid/ethylene glycol (26.5/20/3.5/50)*: | 37.0 mg/m² |
| # copolymer latex of ethyl acrylate/methacrylic acid (80/20): | 3.0 mg/m² |
| # HORDAMER ™ PE02: | 1.0 mg/m² |
| # PAREZ RESIN ™ 707: | 7.0 mg/m² |

* contains 7.1% of Surf. Nr S18 & 1.98% of Surf. Nr S01 vs monomers polymerized

Preparation of a Silver Behenate Dispersion 9000 g of silver behenate were added with stirring to 9000 g of a 10% aqueous solution of Surfactant Nr S02 diluted with 20,146 g of deionized water and the mixture stirred for 30 minutes with a KOTTHOFF™ stirrer. The resulting dispersion was then passed four times through a Type M110F high pressure homogenizer from MICROFLUIDICS™ Corporation at a pressure of 400 bar to obtain a finely divided aqueous silver behenate dispersion.

Preparation of a Tone Modifier Dispersion

The tone modifier dispersion was prepared by first dissolving 8.8 g of K7598 in 71.4 g of deionized water by first adding the gelatin, then allowing the gelatin to swell for 30 minutes and finally heating to 50° C. 20 g of T01 was added with ULTRA-TURRAX™ stirring to this gelatin solution at 50° C., and the stirring continued for a further 5 minutes. Finally the resulting dispersion was pumped through a DYNOMILL™ for 2 hours to produce the final tone modifier dispersion containing: 20% of T01 and 8.8% of K7598.

Preparation of the Silver Behenate Emulsion Layers

The coating dispersions for the thermographic recording materials of INVENTION EXAMPLES 1 to 10 and COMPARATIVE EXAMPLES 1 & 2 were prepared by first dissolving 1.927 g of K7598 in deionized water at 38° C. (for the quantity of water see table 1), then adding with stirring to the warm K7598 solution: first 19.0 g of the silver behenate dispersion, then 5.68 g of the tone modifier dispersion as flakes followed by 15 minutes stirring, then the latex dispersion (for quantity, concentration and type see table 1), then 11.23 g of an aqueous ethanol solution containing 0.92 g of R01 and 0.62 g of boric acid and finally 1.310 g of a 3.7% by weight solution of formaldehyde to produce 60 g of a dispersion containing: 7.47% of silver behenate, 0.75% of Surfactant Nr S02, 4.04% of K7598, 2.98% of polymer latex, 1.53% of R01, 1.03% of boric acid, 1.92% of T01 and 0.08% of formaldehyde.

TABLE 1

| | Quantity | polymer latex | | |
|---|---|---|---|---|
| | of water [g] | number | concentration [%] | weight [g] |
| Comparative Example number | | | | |
| 1 | 11.653 | S11 | 19.4 | 9.200 |
| 2 | 11.653 | S11 | 19.4 | 9.200 |
| Invention Example number | | | | |
| 1 | 14.713 | 1 | 29.1 | 6.140 |
| 2 | 14.903 | 1* | 30.0 | 5.950 |
| 3 | 14.903 | 1# | 30.0 | 5.950 |
| 4 | 14.713 | 1# | 29.1 | 6.140 |
| 5 | 10.723 | 4 | 17.6 | 10.130 |
| 6 | 10.973 | 4ᵃ | 18.1 | 9.880 |
| 7 | 11.083 | 5 | 18.3 | 9.770 |
| 8 | 16.643 | 6 | 42.4 | 4.210 |
| 9 | 16.823 | 7 | 44.2 | 4.040 |
| 10 | 10.683 | 8 | 17.5 | 10.170 |

*pH adjusted to 5.5
pH adjusted to 5
ᵃ= no buffer

The resulting emulsions were then doctor blade-coated to a wet thickness of 60 μm at a blade setting of 100 μm onto the 175 μm thick subbed polyethylene terephthalate support and dried for 10 minutes at 50° C., producing a silver behenate coverage of about 4.0 g/m².

Thermographic Printing

The printer was equipped with a thin film thermal head with a resolution of 300 dpi and was operated with a line time of 19 ms (the line time being the time needed for printing one line). During this line time the printhead received constant power. The average printing power, being the total amount of electrical input energy during one line time divided by the line time and by the surface area of the heat-generating resistors was 1.6 mJ/dot being sufficient to obtain maximum optical density in each of the substantially light-insensitive thermographic recording materials of INVENTION EXAMPLES 1 to 10 and COMPARATIVE EXAMPLES 1 & 2.

The maximum densities, $D_{max}$, and minimum densities, $D_{min}$, of the prints given in table 2 were measured through visible or blue filters with a MACBETH™ TR924 densitometer in the grey scale step corresponding to data levels of 64 and 0 respectively and are given Archivability Test The achivability of prints made with the substantially light-insensitive thermographic recording materials of INVENTION EXAMPLES 1 to 10 and COMPARATIVE EXAMPLES 1 & 2 was evaluated on the basis of the observed changes in minimum density, $D_{min}$, upon heating the prints at 35° C. in a relative humidity (RH) of 80% for 3 days in the dark. The results of these tests are also given in table 2.

Light Box Test

The stability of the image background of the prints made with the substantially light-insensitive thermographic recording materials of INVENTION EXAMPLES 1 to 10 and COMPARATIVE EXAMPLES 1 & 2 was evaluated on the basis of the change in minimum (background) density measured through a blue filter using a MACBETH™ TR924 densitometer upon exposure on top of the white PVC window of a specially constructed light-box placed for 3 days in a VÖTSCH conditioning cupboard set at 30° C. and a relative humidity (RH) of 85%. Only a central area of the window 550 mm long by 500 mm wide was used for mounting the test materials to ensure uniform exposure.

The stainless steel light-box used was 650 mm long, 600 mm wide and 120 mm high with an opening 610 mm long and 560 mm wide with a rim 10 mm wide and 5 mm deep round the opening, thereby forming a platform for a 5 mm thick plate of white PVC 630 mm long and 580 mm wide, making the white PVC-plate flush with the top of the light-box and preventing light loss from the light-box other than through the white PVC-plate. This light-box was fitted with 9 Planilux™ TLD 36W/54 fluorescent lamps 27 mm in diameter mounted length-wise equidistantly from the two sides, with the lamps positioned equidistantly to one another and the sides over the whole width of the light-box and with the tops of the fluorescent tubes 30 mm below the bottom of the white PVC plate and 35 mm below the materials being tested. The results are summarized in table 2.

TABLE 2

| | AgB coverage [g/m²] | Surfactant (s) Nr (s) | [Cl*] ppm | FRESH PRINT $D_{max}$ vis/blue | FRESH PRINT $D_{min}$ vis/blue | Archivability $\Delta D_{min}$ vis/blue after 3d at 35° C./80% RH | Light box: $\Delta D_{min}$ vis/blue after 3d at 30° C./85% RH |
|---|---|---|---|---|---|---|---|
| Comparative example number | | | | | | | |
| 1 | 3.98 | S01, S02, S04, S17, S18 | 2499 | 4.61/4.54 | 0.08/0.11 | 0.07/0.13 | 0.09/0.35 |
| 2 | 4.08 | S01, S02, S04, S17, S18 | 2499 | 4.62/4.48 | 0.06/0.08 | 0.02/0.03 | 0.13/0.20 |
| Invention number | | | | | | | |
| 1 | 3.40 | S01, S02, S18 | 26–66 | 3.47/3.43 | 0.09/0.11 | 0.01/0.02 | 0.03/0.09 |
| 2 | 3.87 | S01, S02, S18 | 23–63 | 4.54/4.36 | 0.08/0.11 | 0.02/0.03 | 0.03/0.08 |
| 3 | 4.24 | S01, S02, S18 | 21–61 | 2.72/2.79 | 0.10/0.13 | 0.00/0.01 | 0.04/0.08 |
| 4 | 4.24 | S01, S02, S18 | 21–61 | 3.65/3.63 | 0.08/0.10 | 0.00/0.01 | 0.04/0.08 |
| 5 | 4.21 | S01, S02, S18 | 21–61 | 4.14/3.75 | 0.09/0.11 | 0.00/0.01 | 0.03/0.06 |
| 6 | 4.69 | S01, S02, S18 | 19–59 | 4.03/3.98 | 0.07/0.09 | 0.00/0.01 | 0.04/0.08 |
| 7 | 4.45 | S01, S02, S18 | 20–60 | 3.01/3.23 | 0.09/0.11 | 0.00/0.01 | 0.03/0.07 |
| 8 | 4.53 | S01, S02, S18 | 20–60 | 4.08/4.14 | 0.06/0.08 | 0.02/0.02 | 0.04/0.07 |
| 9 | 4.40 | S01, S02, S18 | 20–60 | 4.53/4.43 | 0.07/0.10 | 0.02/0.03 | 0.05/0.09 |
| 10 | 5.03 | S01, S02, S18 | 18–58 | 3.14/3.18 | 0.08/0.10 | 0.00/0.01 | 0.03/0.06 |

The results of the archivability and light box tests show that the stability in light box tests of prints made with the substantially light-insensitive thermographic recording materials of INVENTION EXAMPLES 1 to 10 in which Surfactant Nr S02 is used with a chloride ion concentration of less than 40 ppm are superior to those of the substantially light-insensitive thermographic recording material of COMPARATIVE EXAMPLES 1 & 2 in which Surfactant Nr S02 with a chloride ion concentration of less than 40 ppm is present together with the Surfactant Nr S17 with a chloride ion concentration of 84000 ppm from the Latex Nr 09 used in their preparation. These results show that the integral chloride ion concentration of the non-cationic surfactants used is important in determining the stability of the prints prepared with substantially light-insensitive thermographic recording materials.

INVENTION EXAMPLES 11 TO 14

Preparation of Subbing Layers

Subbing Layer Number C1:

A 0.34 mm thick polyethylene terephthalate sheet was first coated to a wet thickness of 7 μm with a composition which after drying and longitudinal and transverse stretching produced a 175 μm thick support coated with a sub-layer with the following composition, expressed as the coating weights of the ingredients present:

| | |
|---|---|
| # terpolymer latex of vinylidene chloride/methyl acrylate/itaconic acid (88/10/2)*: | 162 mg/m² |
| # KIESELSOL ™ 100F: | 38 mg/m² |
| # alkyl sulfonate surfactant (Surfactant Nr. S16): | 0.6 mg/m² |
| # aryl sulfonate surfactant (Surfactant Nr. S04): | 4 mg/m² |

*contains 3% by weight of Surfactant Nr S01 versus monomer polymerized

The 175 μm thick longitudinally stretched polyethylene terephthalate support was then coated on one side with a composition which after drying at 130° C. produced a second sub-layer with the following layer composition, expressed as the coating weights of the ingredients present:

| | |
|---|---|
| # R10985: | 390 mg/m² |
| # KIESELSOL ™ 300F: | 341 mg/m² |
| # PMMA: | 1 mg/m² |
| # an alkylpolyethylene glycol (Surfactant Nr. S09) | 7 mg/m² |
| # aryl sulfonate surfactant (Surfactant Nr. S04): | 13 mg/m² |
| # 4-chloro-3-methylphenol: | 10 mg/m² |
| # 1,2,6-trihydroxyhexane: | 25 mg/m² |

These two sub-layers together form SUBBING LAYER NUMBER C1, which is used in the photographic art as a subbing layer for providing adhesion between a polyethylene terephthalate support and gelatinous silver halide emulsion layers.

Subbing Layer Number 01

A 0.34 mm thick polyethylene terephthalate sheet was coated to a thickness of 0.1 mm with a composition which after drying and longitudinal and transverse stretching produced a 175 μm thick support coated with the following subbing-layer composition of SUBBING LAYER NUMBER 01 expressed as the coating weights of the ingredients present:

| | |
|---|---|
| # terpolymer latex of vinylidene chloride/methyl acrylate/itaconic acid (88/10/2)*: | 162 mg/m² |
| # colloidal silica (KIESELSOL ™ 100F from BAYER): | 38 mg/m² |
| # alkyl sulfonate surfactant (Surfactant Nr. S16): | 0.6 mg/m² |
| # aryl sulfonate surfactant (Surfactant Nr. S04): | 4 mg/m² |

*contains 3% by weight of Surfactant Nr S01 versus monomer polymerized

Subbing Layer Number 02

Subbing Layer as Described for INVENTION EXAMPLES 1 to 10 and COMPARATIVE EXAMPLES 1 & 2.

Preparation of a Silver Behenate Dispersion 1125 g of a 10% aqueous solution of Surfactant Nr S09 and 1500 g of silver behenate were added to 4875 g of deionized water and the mixture stirred for 30 minutes with a HOMOREX™ stirrer. The resulting dispersion was then stirred for 15 minutes with an ULTRA-TURRAX™ stirrer after which it was stored for 24 hours in a refrigerator to allow the foam to dissipate. The dispersion was then stirred for 10 minutes with an ULTRA-TURRAX™ stirrer and passed twice through a GUERIN homogenizer coupled with a Type M110F high pressure homogenizer from MICROFLUIDICS™ Corporation at a pressure of 350 bar to obtain a finely divided aqueous silver behenate dispersion.

A gelatin solution was produced by adding 660 g of K7598 to 2319 g of deionized water, allowing the gelatin to swell for 30 minutes and heating the mixture to 50° C. The gelatin solution was then added to the aqueous silver behenate dispersion with vigorous stirring with a DISSOLVER™, after which the stirring was continued for a further 15 minutes producing a gelatinous aqueous dispersion of silver behenate containing: 14.3% of silver behenate, 1.07% of Surfactant Nr. S09 and 6.28% of K7598.

Preparation of the Silver Behenate Emulsion Layers

The coating dispersion was prepared by adding 324 g of the gelatinous aqueous dispersion of silver behenate to 165.7 g of deionized water, heating the dispersion to 36° C., then adding 81 g of the tone modifier dispersion (produced as described for INVENTION EXAMPLES 1 TO 10 and COMPARATIVE EXAMPLES 1 & 2) as flakes, followed by stirring for 15 minutes before adding with stirring 70.8 g of a 30% latex dispersion of polymer latex nr 1 at pH 5 containing 1% by weight of Surfactant S01 with respect to monomers used in the poymerization, a further 5 minutes stirring was followed by the addition with stirring of 103.24 g of a 7.25% aqueous solution of boric acid at 50° C., 11.01 g of R01 in 20.52 g of ethanol and 15.7 g of a 3.7% aqueous solution of formaldehyde to produce a dispersion containing: 5.85% of silver behenate, 0.44% of Surfactant Nr S09, 3.47% of K7598, 2.68% of polymer latex number 1, 0.0268% of Surfactant Nr 501, 1.39% of R01, 0.94% of boric acid, 2.05% of T01 and 0.07% of formaldehyde.

The resulting emulsion was then doctor blade-coated to a wet thickness of 60 μm with the blade at a setting of 100 μm onto an unsubbed 100 μm thick polyethylene terephthalate support in the case of COMPARATIVE EXAMPLE 1 and a 175 μm thick polyethylene tere-phthalate supports coated with different subbing layers in the cases of INVENTION EXAMPLES 11 to 14 and dried for 10 minutes at 50° C., producing a silver behenate coverage of 3.8 g/m².

Thermographic Evaluation

The thermographic printing for the thermographic recording materials of INVENTION EXAMPLES 11 to 14 was carried out as described for INVENTION EXAMPLES 1 to 10 and COMPARATIVE EXAMPLES 1 & 2.

Image evaluation

The maximum densities, $D_{max}$, and minimum densities, $D_{min}$, of the prints given in table 3 were measured through a blue filter with a MacBeth™ TR924 densitometer in the grey scale step corresponding to data levels of 255 and 0 respectively and are given for the fresh thermographic recording materials of INVENTION EXAMPLES 11 to 14 in table 3.

The archivability tests and light box tests were caried out as described for the thermographic recording materials of INVENTION EXAMPLES 1 to 10 and COMPARATIVE EXAMPLES 1 & 2. The results are also summarized in table 3.

TABLE 3

| Invention example number | AgB cover age [g/m²] | sub-bing layer nr. | Surfactants nrs | [Cl*] ppm | FRESH $D_{max}$ vis/blue | $D_{min}$ vis/blue | Archivability: $\Delta D_{min}$ vis/blue after 3d at 35° C./80% RH | Light box: $\Delta D_{min}$ vis/blue after 3d at 30° C./85% RH) |
|---|---|---|---|---|---|---|---|---|
| 11 | 3.68 | — | S01, S09 | <22 | 3.12/3.23 | 0.07/0.08 | 0.00/0.00 | 0.06/0.11 |
| 12 | 4.13 | Cl | S01, S04 S09, S16 | 62–83 | 3.40/3.55 | 0.08/0.10 | 0.00/0.00 | 0.10/0.28 |
| 13 | 3.56 | 1 | S01, S04 S09, S16 | 44–66 | 2.65/2.71 | 0.08/0.09 | 0.00/0.00 | 0.06/0.14 |
| 14 | 3.87 | 2 | S01, S09 S18 | 29–51 | 3.05/3.13 | 0.08/0.09 | 0.00/0.00 | 0.05/0.12 |

The results of the thermographic evaluation of the thermographic recording material of INVENTION EXAMPLE 11 in which only Surfactant Nrs S01 and S09 were used show lower increases in $D_{min}$ in archivability and light box tests, indicating higher stability, than those for the thermographic recording materials of INVENTION EXAMPLES 12 to 14 which contain Surfactants with high chloride-ion concentrations in addition to surfactant Nrs S01 and S09.

INVENTION EXAMPLES 15 TO 19

Preparation of Silver Behenate Dispersions in an Aqueous Medium in the Absence of Organic Solvent Using a Single Jet Process Aqueous dispersions of the silver behenate types I to V of INVENTION EXAMPLES 15 to 19 were produced as follows:

i) dispersing 102.18 g (0.3M) behenic acid with stirring at 400 rpm with a 100 mm diameter typhoon stirrer in a 250 mm in diameter vessel at 80° C. in a quantity of mL of a 10% solution of Surfactant Mr S02/g behenic acid (see table 4) made up to 1L with deionized water at a temperature of 80° C.;
ii) then adding 150 mL of a 2M aqueous solution of sodium hydroxide with stirring at 400 rpm with a 100 mm diameter typhoon stirrer to the 250 mm in diameter vessel at 60° C. over a period of 10 to 20 minutes to clear solution substantially containing sodium behenate;
iii) then adding a 300 mL of a 1M (or 100 mL of 3M in cases of INVENTION EXAMPLES 13 & 14) aqueous solution of silver nitrate with stirring at 400 rpm with a 100 mm diameter typhoon stirrer to the 250mm in diameter vessel at a temperature of BOC at a particular rate of moles/ moles silver behenate-min (see table 4 for the value for the particular silver behenate type), to convert the sodium behenate completely into silver behenate; and iv) ultrafiltration with a 500000 MW polysulfone cartridge filter at room temperature cassette to concentrate the resulting silver behenate dispersion (final AgB-concentration and residual conductivity in mS/cm are given in table 4).

The volume average particle size as determined by a Coulter LS230 diffractometer is also given in table 4.

TABLE 4

| Invention example number | AgB type | Surfactant Nr | ml 10% sol./g HBeh | Temperature [° C.] | mol AgNO₃ /mol AgB.min | ultrafiltration residual conductivity [mS/cm] | % AgB dispersion | average particle size [µm] |
|---|---|---|---|---|---|---|---|---|
| 15 | I | S02 | 2.28 | 80 | 0.0625 | 4.9 | 23.3 | 0.433 |
| 16 | II | S02 | 2.28 | 80 | 0.0625 | 4.3 | 18.9 | |
| 17 | III | S02 | 2.28 | 80 | 2.25 | | 14.11 | 0.111 |
| 18 | IV | S02 | 4.56 | 80 | 0.0625 | 6.2 | 14.0 | 0.187 |
| 19 | V | S02 | 4.56 | 80 | 0.157 | 6.5 | 14.0 | 0.135 |

These dispersions of silver behenate were directly used in the preparation of thermographic recording materials comprising thermographic elements coated from aqueous media.

Toning Agent Dispersions toner dispersion 01: dispersion of T02 in an aqueous solution of Surfactant Nr 1 containing 30% of T02 and 3% of Surfactant Nr. S02 (added as a dispersion);

Preparation of Thermographic Recording Materials With the Aqueous Silver Behenate-dispersions The thermographic recording materials of INVENTION EXAMPLES 15 to 19 were prepared by first dissolving K7598 in deionized water at 36° C. (see table 5 for quantities), then adding the appropriate Surfactant Nr S02-containing silver behenate emulsion (see table 5 for quantity and concentration), then an aqueous dispersion of Latex Nr 1 with a pH of 5.0 (for quantity see table 5) followed by 5 minutes stirring, then an aqueous toner dispersion (for number and quantity, see table 5), while keeping the dispersion at 36° C. followed by vigorous stirring, then a toner dispersion (see table 5 for type and quantity), then 11.23 g of a 13.7% by weight solution of R01 in ethanol and finally 1.31 g of a 3.66% by weight aqueous solution of formaldehyde.

TABLE 5

| Invention example number | water [g] | K7598 [g] | AgB dispersion. conc [%] | wt. [g] | Latex Nr 1 conc [%] | wt. [g] | toner nr | dispersion wt. [g] |
|---|---|---|---|---|---|---|---|---|
| 15 | 22.66 | 2.25 | 23.25 | 19.36 | 30 | 5.58 | 01 | 3.61 |
| 16 | 10.58 | 2.26 | 18.9 | 23.68 | 30 | 5.57 | 02 | 5.38 |
| 17 | 10.12 | 2.25 | 14.11 | 31.90 | 30 | 5.58 | 01 | 3.61 |
| 18 | 9.90 | 2.25 | 14.0 | 32.13 | 30 | 5.58 | 01 | 3.61 |
| 19 | 9.82 | 2.25 | 14.0 | 32.20 | 30 | 5.58 | 01 | 3.61 |

The resulting silver behenate emulsions were then doctor blade-coated onto a 175 μm thick subbed (subbing layer as described for INVENTION EXAMPLES 1 to 10 and COMPARATIVE EXAMPLES 1 & 2) polyethylene terephthalate support to produce the coating weights of silver given in table 6.

Thermographic Evaluation

The thermographic recording materials of INVENTION EXAMPLES 15 to 19 were printed and the prints evaluated as described for INVENTION EXAMPLES 1 to 10 and COMPARATIVE EXAMPLES 1 & 2. The maximum and minimum densities of the prints obtained with the thermographic recording materials of INVENTION EXAMPLES 15 to 19 measured through a blue filter with a MACBETH™ TR924 densitometer for grey scale steps corresponding to data levels of 255 and 0 respectively are also given in table 6.

Archivability Test

The achivability of prints made with the thermographic recording materials of INVENTION EXAMPLES 15 to 19 was evaluated on the basis of the observed changes in minimum density upon heating the prints at 57° C. in a relative humidity (RH) of 34% for 3 days in the dark. The results of these tests are given in table 6.

Light Box Test

The light box tests on the thermographic recording materials of INVENTION EXAMPLES 15 to 19 were carried out as described for INVENTION EXAMPLES 1 to 10 and COMPARATIVE EXAMPLES 1 & 2 and the results are summarized in table 6.

TABLE 6

| Invention Example number | AgB type | AgB coverage [g/m²] | Surfactants Nrs | [Cl*] ppm | fresh print characteristics $D_{max}$ blue | $D_{min}$ blue | archivability: $\Delta D_{min}$ blue after 3d at 57° C./ 34% RH) | light box: $\Delta D_{min}$ blue after 3d at 30° C./ 85% RH) |
|---|---|---|---|---|---|---|---|---|
| 15 | I | 2.66 | S01, S02, S18 | 17–57 | 4.41 | 0.14 | −0.01 | 0.03 |
| 16 | II | 3.98 | S01, S02, S18 | 12–52 | 3.56 | 0.11 | +0.01 | 0.04 |
| 17 | III | 3.61 | S01, S02, S18 | 13–53 | 3.27 | 0.12 | −0.03 | −0.01 |
| 18 | IV | 3.82 | S01, S02, S18 | 6–46 | 3.02 | 0.11 | −0.01 | 0.00 |
| 19 | V | 4.19 | S01, S02, S18 | 6–46 | 3.16 | 0.13 | −0.02 | −0.01 |

The results of the thermographic evaluation of the thermographic recording material of INVENTION EXAMPLES 15 to 19 in which Surfactant Nrs S01, S02 and S08 were used show lower increases in $D_{min}$ in archivability and light box tests, indicating higher stability, than those for the thermographic recording materials of COMPARATIVE EXAMPLES 3 & 4 which contain Surfactants with higher chloride-ion concentrations (S16 and S12 respectively) were used in addition to Surfactant Nrs S01 and S08.

INVENTION EXAMPLE 20

The photothermographic recording material of INVENTION EXAMPLE 20 was produced using a silver behenate dispersion prepared as described in INVENTION EXAMPLE 19 for silver behenate type V except that no ultrafiltration was carried out and that the concentration of silver behenate in the dispersion was 8.15% by weight instead of 14.0% by weight.

A photothermographic coating dispersion was then obtained by mixing with stirring 7.5 g of the silver behenate dispersion with 4 g of an 0.44% by weight aqueous solution of potassium iodide, then 2 g of a 20% by weight aqueous dispersion of Latex Nr 01, then 0.64 g of a 5.6% by weight aqueous solution of phthalazine and finally with 2 g of a 5.6% by weight aqueous solution of R02. The resulting coating dispersion was then doctor blade-coated to a wet thickness of 120 μm onto a subbed (subbing layer as described for INVENTION EXAMPLES 1 to 10 and COMPARATIVE EXAMPLES 1 & 2) polyethylene terephthalate support having a thickness of 100 μm to obtain, after drying for 1 hour at 50° C., a photothermographic recording material with a silver behenate coating weight of 3.28 g/m² and a silver iodide coating weight of 0.12 g/m². The concentration of chloride-ions in the the non-cationic surfactants present was 7–47 ppm.

The photothermographic recording material of INVENTION EXAMPLE 20 was then exposed to ultra-violet light through a test original in contact with the material in an AGFA-GEVAERT™ DL 1000 exposure apparatus followed by heating on a heated metal block for 5s at 100° C. to produce a very good image with a high contrast.

INVENTION EXAMPLE 21

The photothermographic recording material of INVENTION EXAMPLE 21 was produced using the silver behenate dispersion described in INVENTION EXAMPLE 20. A photothermographic coating dispersion was then obtained as described for INVENTION EXAMPLE 20 except that 4 g of 0.97% by weight aqueous solution of calcium iodide was used instead of 4 g of an 0.44% by weight aqueous solution of potassium iodide. The resulting coating dispersion was then doctor blade-coated to a wet thickness of 120 μm onto a subbed (subbing layer as described for INVENTION EXAMPLES 1 to 10 and COMPARATIVE EXAMPLES 1 & 2) polyethylene terephthalate support having a thickness of 100 μm to obtain, after drying for 1 hour at 50° C., a photothermographic recording material with a silver behenate coating weight of 3.17 g/m² and a silver iodide coating weight of 0.11 g/m². The concentration of chloride-ione in the non-cationic surfactants present was 8–46 ppm.

The photothermographic recording material INVENTION EXAMPLE 21 was then exposed and thermally developed as described above for INVENTION EXAMPLE 20 to produce a very good image with a high contrast.

INVENTION EXAMPLES 22 TO 25 &
COMPARATIVE EXAMPLES 3 & 4

Preparation of Silver Behenate Dispersions in an Aqueous Medium in the Absence of Organic Solvent Using a Single Jet Process Aqueous dispersions of the silver behenate types VI to IX of INVENTION EXAMPLES 22 to 25 and of silver behenate types X & XI of COMPARATIVE EXAMPLES 3 & 4 respectively were produced as described for silver behenate types I to V of INVENTION EXAMPLES 15 to 19 except as mentioned in table 7 below. The volume average particle size as determined by a Coulter LS230 diffractometer is also given in table 7.

These dispersions of silver behenate were directly used in the preparation of thermographic recording materials comprising thermographic elements coated from aqueous media.

Preparation of Coating Dispersion 3.45 g of K17881 was allowed to swell for 30 minutes in 4.6 g of a 5% aqueous solution of adipic acid adjusted to pH 5.3 with ammonia diluted with water (see table 8 for quantity) and the swollen gelatin heated up to 36° C. The following ingredients were then added with stirring: 4.875 of the tone modifier dispersion used in INVENTION EXAMPLES 1 to 10 and COMPARATIVE EXAMPLES 1 & 2 were added, followed by 5 minutes stirring before the silver behenate dispersion, at a temperature of 36° C., was added first about 2 g then stirring for 5 minutes before adding the rest (for quantity, silver behenate concentration & nature of the dispersion agent see table 8), followed by 10 minutes stirring before 11.150 g of an aqueous solution containing 2.78% of boric acid, 8.17% of R01 and 15.23% of ethanol was added was added and finally 1 g of an aqueous solution containing 19.2% of formaldehyde and 6.75% of methanol was added followed by 5 minutes stirring.

TABLE 7

| | AgB type | Surfactant Nr | g./g Hbeh | Temperature [° C.] | mol AgNO₃/ mol AgB.min | ultrafiltration residual conductivity [mS/cm] | % AgB dispersion | average particle size [μm] |
|---|---|---|---|---|---|---|---|---|
| Invention example number | | | | | | | | |
| 22 | VI | S02 | 0.395 | 80 | $6.25 \times 10^{-3}$ | 2.20 | 22.46 | 0.459 |
| 23 | VII | S05 | 0.362 | 80 | $6.25 \times 10^{-3}$ | 1.9 | 18.4 | 0.463 |
| 24 | VIII | S05 | 0.362 | 80 | $6.25 \times 10^{-3}$ | 1.4 | 17.5 | 0.260 |
| 25 | IX | S01 | 0.403 | 80 | $6.25 \times 10^{-3}$ | 1.9 | 23.1 | 0.615 |
| Comparative example number | | | | | | | | |
| 3 | X | S18 | 0.715 | 80 | $6.25 \times 10^{-3}$ | 1.8 | 16.4 | 0.438 |
| 4 | XI | S12 | 0.440 | 80 | $6.25 \times 10^{-3}$ | 2.6 | 19.4 | — |

TABLE 8

| | AgB type | quantity of deionized water [g] | AgB dispersion Surfactant Nr | g Surfactant/ g AgB | AgB conc [wt. %] | quantity of AgB dispersion [g] |
|---|---|---|---|---|---|---|
| Invention example number | | | | | | |
| 22 | VI | 12.825 | S02 | 0.128 | 22.46 | 21.90 |
| 23 | VII | 7.875 | S05 | 0.21 | 18.4 | 26.85 |
| 24 | VIII | 6.525 | S05 | 0.17 | 17.5 | 28.20 |

TABLE 8-continued

| | AgB type | quantity of deionized water [g] | AgB dispersion | | | |
|---|---|---|---|---|---|---|
| | | | Surfactant Nr | g Surfactant/ g AgB | AgB conc [wt. %] | quantity of AgB dispersion [g] |
| 25 Comparative example number | IX | 13.325 | S01 | 0.22 | 23.1 | 21.40 |
| 3 | X | 4.525 | S18 | 0.31 | 16.4 | 30.20 |
| 4 | XI | 9.325 | S12 | 0.22 | 19.4 | 25.40 |

The resulting silver behenate emulsions were then doctor blade-coated onto a 175 μm thick polyethylene terephthalate support subbed with the subbing layer described for INVENTION EXAMPLES 1 to 10 and COMPARATIVE EXAMPLES 1 & 2 to produce the coating weights of silver given in table 9.

Thermographic Evaluation

The thermographic recording materials of INVENTION EXAMPLES 22 to 25 and COMPARATIVE EXAMPLES 3 & 4 were printed and the prints evaluated as described for INVENTION EXAMPLES 1 to 10 and COMPARATIVE EXAMPLES 1 & 2. The maximum and minimum densities of the prints obtained with the thermographic recording materials of INVENTION EXAMPLES 22 to 25 and COMPARATIVE EXAMPLES 3 & 4 measured through a blue filter with a MACBETH™ TR924 densitometer for grey scale steps corresponding to data levels of 255 and 0 respectively are also given in Table 9. The archivability tests and light box tests were carried out on the thermographic recording materials of INVENTION EXAMPLES 22 to 25 and COMPARATIVE EXAMPLES 3 & 4 as described for INVENTION EXAMPLES 1 to 10 and COMPARATIVE EXAMPLES 1 & 2. The results are summarized in table 9.

The results of the thermographic evaluation of the thermographic recording material of INVENTION EXAMPLES 22 to 25 show lower increases in $D_{min}$ in archivability and light box tests, indicating higher stability, than those for the thermographic recording materials of COMPARATIVE EXAMPLES 3 & 4 which contain Surfactants with high chloride-ion concentrations (S18 and S12 respectively) in addition to Surfactant Nrs S01 and S08.

INVENTION EXAMPLES 26 TO 29 & COMPARATIVE EXAMPLES 5 TO 10

Preparation of Silver Behenate Dispersions

Silver behenate was added with stirring to an aqueous solution of different surfactants (for surfactant used see table 10) and the mixtures stirred for 30 minutes with a KOTTHOFF™ stirrer. The resulting dispersions were then ball milled to obtain a finely divided aqueous silver behenate

TABLE 9

| AgB coverage [g/m²] | Surfactant | | fresh | | Archivability ($\Delta D_{max}/\Delta D_{min}$) | Light box $\Delta D_{max}/\Delta D_{min}$ |
|---|---|---|---|---|---|---|
| | Nr | [Cl*] ppm | $D_{max}$ blue | $D_{min}$ blue | blue) after 3d/35° C./80% RH | (blue) after 3d/30° C./85% RH |
| Invention example number | | | | | | |
| 22  4.43 | S01, S02, S18 | 16–56 | 2.74 | 0.08 | +0.78/+0.02 | +0.23/+0.02 |
| 23  3.90 | S01, S05, S18 | 11–51 | 3.89 | 0.08 | +0.42/+0.02 | +0.27/+0.02 |
| 24  4.19 | S01, S05, S18 | 13–52 | 3.95 | 0.08 | +0.35/+0.01 | +0.07/+0.01 |
| 25  3.64 | S01, S18 | 11–61 | 4.08 | 0.08 | +0.25/+0.01 | −0.01/+0.01 |
| Comparative example number | | | | | | |
| 3  4.40 | S01, S18 | 3440 | 4.24 | 0.09 | +0.14/+0.01 | +0.12/+0.41 |
| 4  4.95 | S01, S12, S18 | 6389 | 4.21 | 0.10 | +0.20/+0.07 | +0.12/+0.03 | dispersion with the quantities of surfactant with respect to silver behenate given in table 10.

TABLE 10

| | Surfactant | | AgB-concentration in |
|---|---|---|---|
| | Nr | g/g AgB | dispersion [% by weight] |
| Invention example number | | | |
| 26 | S02 | 0.1 | 20.7 |
| 27 | S01 | 0.1 | 20.15 |
| 28 | S05 | 0.1 | 19.44 |
| 29 | S03 | 0.1 | 19.81 |
| Comparative example number | | | |
| 5 | S16 | 0.1 | 20.16 |
| 6 | S11 | 0.1 | 19.6 |
| 7 | S18 | 0.1 | 19.71 |
| 8 | S17 | 0.1 | 20.64 |
| 9 | S12 | 0.1 | 20.81 |
| 10 | S15 | 0.1 | 20.16 |

Preparation of Coating Dispersion 3.56 g of K17881 was allowed to swell in water (see table 11 for quantity) for 30 minutes and the swollen gelatin was heated up to 36° C. The following ingredients were then added with stirring: 4.434 g of an aqueous dispersion of 6.63% of K7598 and 13.37% of phthalazinone, the resulting solution was then stirred for an additional 5 minutes before the silver behenate dispersion, at a temperature of 36° C., was added first about 2 g then stirring for 5 minutes before adding the rest (for quantity, silver behenate concentration & nature of the dispersion agent see table 11), then 11.150 g of an aqueous solution containing 2.78% of boric acid, 8.17% of R01 and 15.23% of ethanol was added and finally 1 g of an aqueous solution containing 19.2% of formaldehyde and 6.75% of methanol was added followed by 5 minutes stirring.

TABLE 11

| | quantity of deionized water [g] | AgB dispersion | | |
|---|---|---|---|---|
| | | Surfactant Nr | concentration (% by wt.) | quantity [g] |
| Invention example number | | | | |
| 26 | 15.996 | S02 | 20.7 | 23.750 |
| 27 | 15.346 | S01 | 20.15 | 24.40 |
| 28 | 14.446 | S05 | 19.44 | 25.30 |
| 29 | 14.931 | S03 | 19.81 | 24.815 |
| Comparative example number | | | | |
| 5 | 15.346 | S16 | 20.16 | 24.40 |
| 6 | 14.946 | S11 | 19.8 | 24.80 |
| 7 | 14.746 | S18 | 19.71 | 25.00 |
| 8 | 15.896 | S17 | 20.64 | 23.85 |
| 9 | 36.121 | S12 | 20.81 | 23.625 |
| 10 | 15.371 | S15 | 20.16 | 24.375 |

The resulting silver behenate emulsions were then doctor blade-coated onto a 175 μm thick subbed polyethylene terephthalate support to produce the coating weights of silver given in table 12.

Thermographic Evaluation

The thermographic recording materials of INVENTION EXAMPLES 26 to 29 and COMPARATIVE EXAMPLES 5 to 10 were printed and the prints evaluated as described for INVENTION EXAMPLES 1 to 10 and COMPARATIVE EXAMPLES 1 & 2. The maximum and minimum densities of the prints obtained with the thermographic recording materials of INVENTION EXAMPLES 26 to 29 and COMPARATIVE EXAMPLES 5 to 10 measured through a blue filter with a MACBETH™ TR924 densitometer for grey scale steps corresponding to data levels of 255 and 0 respectively are also given in table 12. The archivability tests and light box tests were carried out on the thermographic recording materials of INVENTION EXAMPLES 26 to 29 and COMPARATIVE EXAMPLES 5 to 10 as described for INVENTION EXAMPLES 1 to 10 and COMPARATIVE EXAMPLES 1 & 2. The results are summarized in table 12.

TABLE 12

| | AgB coverage [g/m²] | Surfactant | | fresh | | Archivability $\Delta D_{max}/D_{min}$ blue after 3d | Light box: $\Delta D_{max}/\Delta D_{min}$ blue after |
|---|---|---|---|---|---|---|---|
| | | Nr | [Cl*] [ppm] | $D_{max}$ blue | $D_{min}$ blue | at 35° C./ 80% RH | 3d at 30° C./ 85% RH |
| Invention example number | | | | | | | |
| 26 | 3.87 | S01, S02, S18 | 23–63 | 4.12 | 0.07 | −0.01/−0.01 | −0.09/+0.02 |
| 27 | 3.82 | S01, S18, | 23–73 | 4.35 | 0.05 | −0.02/+0.00 | 0.00/+0.03 |
| 29 | 6.15 | S01, S05, S18 | 18–54 | 4.24 | 0.06 | +0.03/+0.00 | +0.01/+0.02 |
| 29 | 5.11 | S01, S03, S18 | 18–57 | 4.22 | 0.06 | −0.05/−0.01 | −0.12/+0.03 |
| Comparative example number | | | | | | | |
| 5 | 5.66 | S01, S16, S18 | 16916 | 4.05 | 0.11 | −0.14/−0.02 | −0.31/+0.11 |
| 6 | 4.11 | S01, S11, S18 | 1609 | 4.03 | 0.08 | −0.03/+0.00 | −0.22/+0.05 |
| 7 | 4.85 | S01, S18 | 3437 | 4.07 | 0.06 | +0.09/+0.02 | −0.11/+0.08 |

TABLE 12-continued

| | AgB cover- | Surfactant | | fresh | | Archivability $\Delta D_{max}/D_{min}$ blue after 3d | Light box: $\Delta D_{max}/\Delta D_{min}$ blue after |
|---|---|---|---|---|---|---|---|
| | age [g/m$^2$] | Nr | [Cl*] [ppm] | $D_{max}$ blue | $D_{min}$ blue | at 35° C./ 80% RH | 3d at 30° C./ 85% RH |
| 8 | 3.90 | S01, S17, S18 | 83333 | 4.13 | 0.09 | −0.30/+0.02 | −0.18/+0.15 |
| 9 | 4.06 | S01, S12, S18 | 6368 | 3.62 | 0.08 | −0.25/+0.01 | −0.44/+0.04 |
| 10 | 3.82 | S01, S15, S18 | 3600 | 4.25 | 0.06 | +0.07/+0.04 | −0.01/+0.06 |

The results of the thermographic evaluation of the thermographic recording material of INVENTION EXAMPLES 26 to 29 show lower increases in $D_{min}$ in archivability and light box tests, indicating higher stability, than those for the thermographic recording materials of COMPARATIVE EXAMPLES 5 to 10 which contain Surfactants with high chloride-ion concentrations (S16, S11, S18, S17, S12 and S15 respectively) in addition to Surfactant Nre S01 and S09 from the subbing layer of the support.

INVENTION EXAMPLES 30 TO 32

Preparation of Silver Behenate Dispersions

Silver behenate was added with stirring to an aqueous solution of different surfactants (for surfactant used see table 13) and the mixtures stirred for 30 minutes with a KOTTHOFF™ stirrer. The resulting dispersions were then ball-milled to obtain a finely divided aqueous silver behenate dispersion with the quantities of surfactant with respect to silver behenate given in table 13.

TABLE 13

| Invention example number | Surfactant Nr | g 10% sol/g AgB | AgB-concentration in dispersion [% by weight] |
|---|---|---|---|
| 30 | S02 | 1 | 23.59 |
| 31 | S05 | 1 | 19.6 |
| 32 | S03 | 1 | 19.7 |

2.78 of K7598 was allowed to swell in water (see table 14 for quantity) for 30 minutes and the swollen gelatin was heated up to 36° C. The following ingredients were then added with stirring; the silver behenate dispersion (for quantity, silver behenate concentration & quantity and nature of the dispersion agent see table 14) at a temperature of 36° C., the pH of the dispersion was then adjusted to 5.0 to 5.5, then 7 g of a 30% by weight dispersion of Latex Nr 1 was added, then 3.675 g of flakes of toning agent dispersion (containing 20% of K7598 and 10% of T02), then after at least 10 minutes stirring 12.85 g of then 11.150 g of an aqueous solution containing 5.55% of boric acid, 8.17% of R01 and 15.23% of ethanol was added and finally 1.390 g of a 3.67% by weight solution of formaldehyde.

TABLE 14

| Invention | quantity of | | silver behenate dispersion | | |
|---|---|---|---|---|---|
| example number | deionized water [g] | Quantity [g] | AgB-conc. [wt %] | Surfactant Nr | g Surfactant/ g AgB |
| 30 | 10.045 | 22.260 | 25.95 | S02 | 0.1 |
| 31 | 6.055 | 26.250 | 22.0 | S05 | 0.1 |
| 32 | 6.055 | 26.250 | 22.0 | S03 | 0.1 |

The resulting silver behenate emulsions were then doctor blade-coated onto a 175 μm thick subbed (subbing layer 1 described for INVENTION EXAMPLE 14) polyethylene terephthalate support to produce the coating weights of silver given in table 15.

Thermographic Evaluation

The thermocraphic recording materials of INVENTION EXAMPLES 30 to 32 were printed and the prints evaluated as described for INVENTION EXAMPLES 1 to 10 and COMPARATIVE EXAMPLES 1 & 2. The maximum and minimum densities of the prints obtained with the thermographic recording materials of INVENTION EXAMPLES 30 to 32 measured through a blue filter with a MACBETH™ TR924 densitometer for grey scale steps corresponding to data levels of 255 and 0 respectively are also given in table 15.

The archivability tests and light box tests were carried out on the thermographic recording materials of INVENTION EXAMPLES 30 to 32 as described for INVENTION EXAMPLES 1 to 10 and COMPARATIVE EXAMPLES 1 & 2. The results are summarized in table 15.

TABLE 15

| Invention example number | AgB cover- age [g/m$^2$] | Surfactants Nrs | [Cl*] [ppm] | fresh $D_{max}$ blue | $D_{min}$ blue | Archivability $\Delta D_{max}/\Delta D_{min}$ blue after 3d at 35° C./80% RH | Light box: $\Delta D_{max}/\Delta D_{min}$ blue after 3d at 30° C./85% RH |
|---|---|---|---|---|---|---|---|
| 30 | 5.36 | S01, S02, S04, S16 | 24–64 | 4.40 | 0.12 | +0.30/−0.03 | +0.19/+0.07 |
| 31 | 5.71 | S01, S04, S05, S16 | 22–62 | 4.38 | 0.13 | +0.25/+0.03 | +0.25/+0.07 |
| 32 | 5.34 | S01, S03, S04, S16 | 24–64 | 4.31 | 0.20 | +0.01/+0.01 | +0.24/+0.05 |

The results of the thermographic evaluation of the thermographic recording material of INVENTION EXAMPLES 30 to 32 show low increases in $D_{min}$ in archivability and light box tests, indicating high stability, particularly in view of the subbing layer used which contains S16 with a very high concentration of chloride-ion. This indicates the benefit of using surfactants in the thermosensitive element with low chloride-ion concentrations.

INVENTION EXAMPLES 33 TO 36

Preparation of Silver Behenate Dispersions

Silver behenate was added with stirring to an aqueous solution of different surfactants (for surfactant used see table 16) and the mixtures stirred for 30 minutes with a KOT-THOFF™ stirrer. The resulting dispersions were then ball-milled to obtain a finely divided aqueous silver behenate dispersion with the quantities of surfactant with respect to silver behenate given in table 16.

TABLE 16

| Invention example number | Surfactant Nr | C1* concentration (ppm) | g 10% sol /g AgB | AgB-concentration in dispersion [% by weight] |
|---|---|---|---|---|
| 33 | S19 | <20 | 1 | 18.55 |
| 34 | S20 | 50 | 1 | 18.55 |
| 35 | S21 | 200 | 1 | 18.4 |
| 36 | S21 | 500 | 1 | 18.55 |

2.23 g of K7598 was allowed to swell in 15.986 g of deionized water for 30 minutes and the swollen gelatin was heated up to 36° C. The following ingredients were then added with stirring: 4.434 g of a 20% aqueous solution of phthalazinone followed by 5 minutes stirring, then 22.20 g of the silver behenate dispersion at a temperature of 36° C. (for the surfactant used see table 16) followed by 10 minutes stirring, then 11.150 g of an aqueous solution containing 5.55% of boric acid, 8.17% of R01 and 15.23% of ethanol was added and finally 1.0 g of an aqueous solution containing 19.2% of formaldehyde and 6.75% of methanol.

The resulting silver behenate dispersions were then doctor blade-coated onto a 175 μm thick subbed (subbing layer 1 described for INVENTION EXAMPLE 14) polyethylene terephthalate support to produce the coating weights of silver given in table 17.

Thermographic Evaluation

The thermographic recording materials of INVENTION EXAMPLES 33 to 36 were printed and the prints evaluated as described for INVENTION EXAMPLES 1 to 10 and COMPARATIVE EXAMPLES 1 & 2. The maximum and minimum densities of the prints obtained with the thermographic recording materials of INVENTION EXAMPLES 33 to 36 measured through a blue filter with a MACBETH™ TR924 densitometer for grey scale steps corresponding to data levels of 255 and 0 respectively are also given in table 17.

The light box tests were carried out on the thermographic recording materials of INVENTION EXAMPLES 33 to 36 as described for INVENTION EXAMPLES 1 to 10 and COMPARATIVE EXAMPLES 1 & 2. The results are summarized in table 17.

TABLE 17

| Invention example number | AgB cover age [g/m²] | Surfactants Nr | [Cl*] [ppm] | fresh $D_{max}$ blue | fresh $D_{min}$ blue | Light box: $\Delta D_{max}/\Delta D_{min}$ blue after 3d at 30° C./85% RH |
|---|---|---|---|---|---|---|
| 33 | 3.74 | S01, S04, S16, S19 | 35–54 | 2.55 | 0.05 | +0.07/+0.02 |
| 34 | 3.66 | S01, S04, S16, S20 | 84 | 2.43 | 0.05 | +0.22/+0.02 |
| 35 | 3.66 | S01, S04, S16, S21 | 230 | 2.63 | 0.05 | −0.07/+0.01 |
| 36 | 3.40 | S01, S04, S16, S22 | 524 | 2.26 | 0.05 | +0.14/+0.01 |

The results of the thermographic evaluation of the thermographic recording material of INVENTION EXAMPLES 33 to 36 show low increases in $D_{min}$ in archivability, indicating high stability, particularly in view of the subbing layer used which contains S16 with a very high concentration of chloride-ion. There is no significant diffference in light stability between the thermographic recording materials of INVENTION EXAMPLES 33 to 36 indicating that up to a concentration of 524 ppm the total chloride ion concentration in the surfactants present has no significant influence on the light stability of thermographic recording materials.

Having described in detail preferred embodiments of the current invention, it will now be apparent to those skilled in the art that numerous modifications can be made therein without departing from the scope of the invention as defined in the following claims.

What is claimed is:

1. A substantially light-insensitive thermographic recording material substantially exclusive of cationic surfactants in which at least one non-cationic surfactant is present, said thermographic recording material comprising a support and a thermosensitive element containing a substantially light-insensitive organic silver salt, a reducing agent therefor in thermal working relationship therewith and a binder, wherein all said non-cationic surfactants present in the thermographic recording material together have a non-fluoro-halide ion concentration of 1500 ppm or less.

2. Substantially light-insensitive thermographic recording material according to claim 1 wherein all said non-cationic surfactants present together have a non-fluoro-halide ion concentration of 1000 ppm or less.

3. Substantially light-insensitive thermographic recording material according to claims 1, wherein all said non-cationic surfactants present together have a metal ion concentration of 500 ppm or less.

4. Substantially light-insensitive thermographic recording material according to claims 1, wherein all said non-cationic surfactants present together have a metal ion concentration of 200 ppm or less.

5. Substantially light-insensitive thermographic recording material according to claim 1, wherein said non-fluoro halide ion is a chloride ion.

6. Substantially light-insensitive thermographic recording material according to claim 1, wherein said binder is gelatin.

7. Substantially light-insensitive thermographic recording material according to claim 1, wherein said thermosensitive element is provided with a protective layer.

8. Substantially light-insensitive thermographic recording material according to claim 7, wherein said protective layer contains a non-cationic surfactant.

9. Substantially light-insensitive thermographic recording material according to claim 1, wherein a subbing layer is provided between said thermosensitive element and said support.

10. Substantially light-insensitive thermographic recording material according to claim 9, wherein said subbing layer contains a non-cationic surfactant.

11. Substantially light-insensitive thermographic recording material according to claim 1, wherein said thermographic recording material is a black and white thermographic recording material.

12. Substantially light-insensitive thermographic recording material according to claim 1, wherein all said non-cationic surfactants present together have an alkali metal ion concentration of 200 ppm or less.

* * * * *